United States Patent [19]

Garnic et al.

[11] Patent Number: 5,354,310
[45] Date of Patent: Oct. 11, 1994

[54] EXPANDABLE TEMPORARY GRAFT

[75] Inventors: J. Daniel Garnic, LaCanada, Calif.; Ernesto Avellanet, Miami Lakes, Fla.; Michael L. O'Hara, Salt Lake City, Utah

[73] Assignee: Cordis Corporation, Miami Lakes, Fla.

[21] Appl. No.: 34,253

[22] Filed: Mar. 22, 1993

[51] Int. Cl.⁵ ............................................. A61M 29/00
[52] U.S. Cl. ........................................ 606/198; 623/1; 623/12
[58] Field of Search ........................ 606/108, 191, 198; 623/1, 12; 604/107, 104, 105

[56] References Cited

U.S. PATENT DOCUMENTS

| | | | |
|---|---|---|---|
| 3,517,128 | 6/1970 | Hines | 606/198 |
| 4,140,126 | 2/1979 | Choudbury | |
| 4,562,596 | 1/1986 | Kornberg | |
| 4,577,631 | 3/1986 | Kreamer | |
| 4,723,549 | 2/1988 | Wholey et al. | 606/194 |
| 4,733,665 | 3/1988 | Palmaz | |
| 4,787,899 | 11/1988 | Lazarus | 606/108 |
| 4,830,003 | 5/1989 | Wolff et al. | |
| 4,921,484 | 5/1990 | Hillstead | |
| 4,954,126 | 9/1990 | Wallsten | |
| 5,034,001 | 7/1991 | Garrison et al. | |
| 5,064,434 | 11/1991 | Haber | 606/198 |

FOREIGN PATENT DOCUMENTS 518704 12/1992 European Pat. Off. ............ 623/1

OTHER PUBLICATIONS

Mirich et al., "Percutaneously Placed Endovascular Grafts for Aortic Aneurisms Feasibility Study", Radiology, 1989, vol. 170, pp. 1033-1037.

Clugston et al., "Flow Support Catheter for Prolonged Maintenance of Coronary Blood Flow", Wiley-Liss, Inc., 1991.

Oz et al., "Twelve-Year Experience with Intraluminal Sutureless Ringed Graft Replacement of the Descending Thoracic and Thoracoabdominal Aortic", Journal of Vascular Surgery, vol. 11, No. 2, Feb. 1990.

Matsumae et al., "An Experimental Study of a New Sutureless Intraluminal Graft with an Elastic Ring that Can Attach Itself to the Vessel Wall", Journal of Vascular Surgery, Jul. 1988.

Filcard Temporary Filter no date.

Primary Examiner—Tamara L. Graysay
Attorney, Agent, or Firm—Watts, Hoffmann, Fisher & Heinke

[57] ABSTRACT

A medical implant particularly suited for stabilizing an aortic aneurism. The implant is intended to be inserted into the patient and expanded to bring a graft into contact with inner wall linings of a blood vessel. The act of expanding the device also causes the device to separate from an insertion catheter used in placing the device. A preferred implant includes two plastic tubes spaced apart by a wire mesh that expands as the two tubes are moved closer together. A flexible graft covers the wire mesh so that as the mesh expands, the graft contacts inner wall linings of a blood vessel, typically the aortic artery.

14 Claims, 3 Drawing Sheets

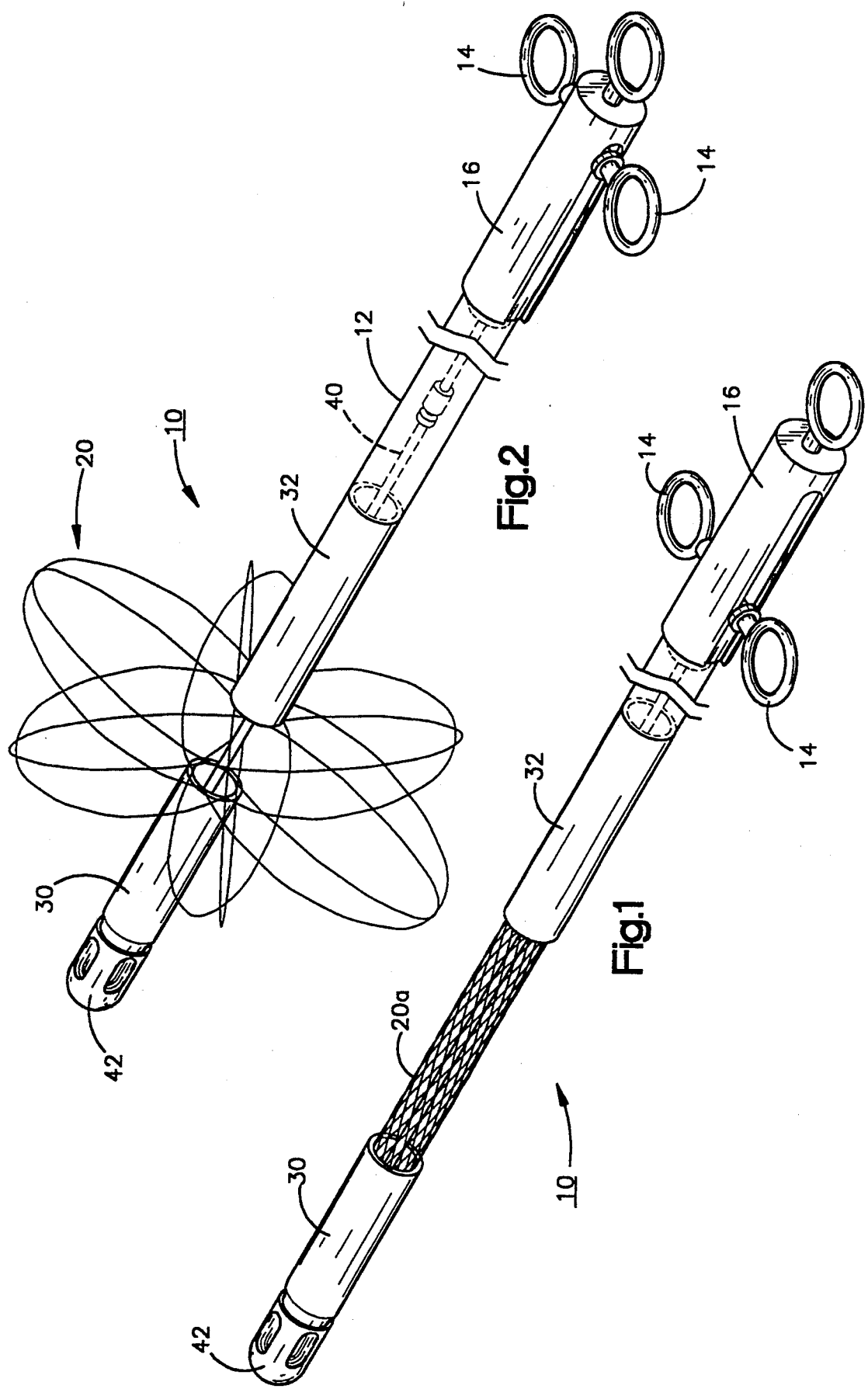

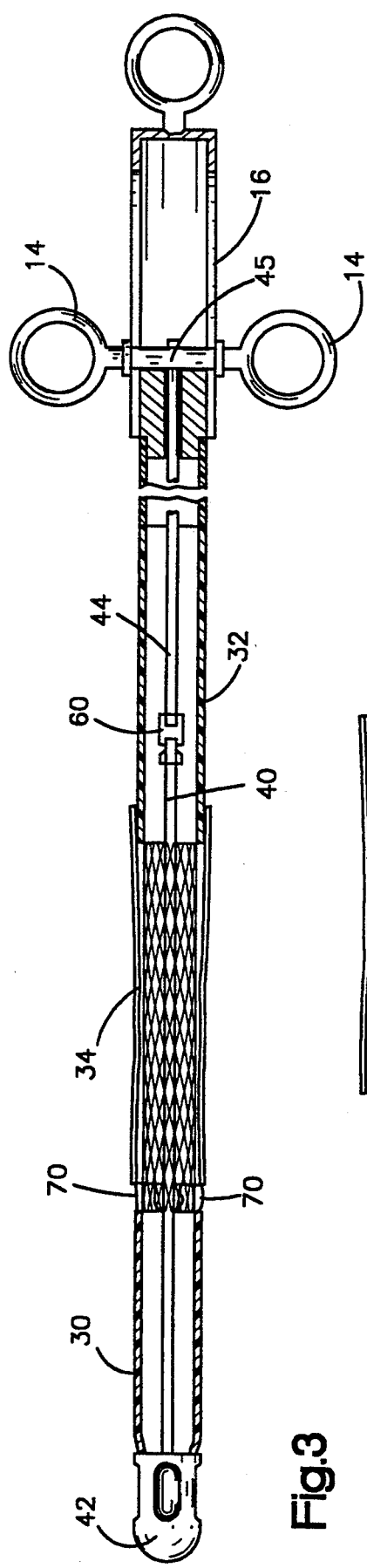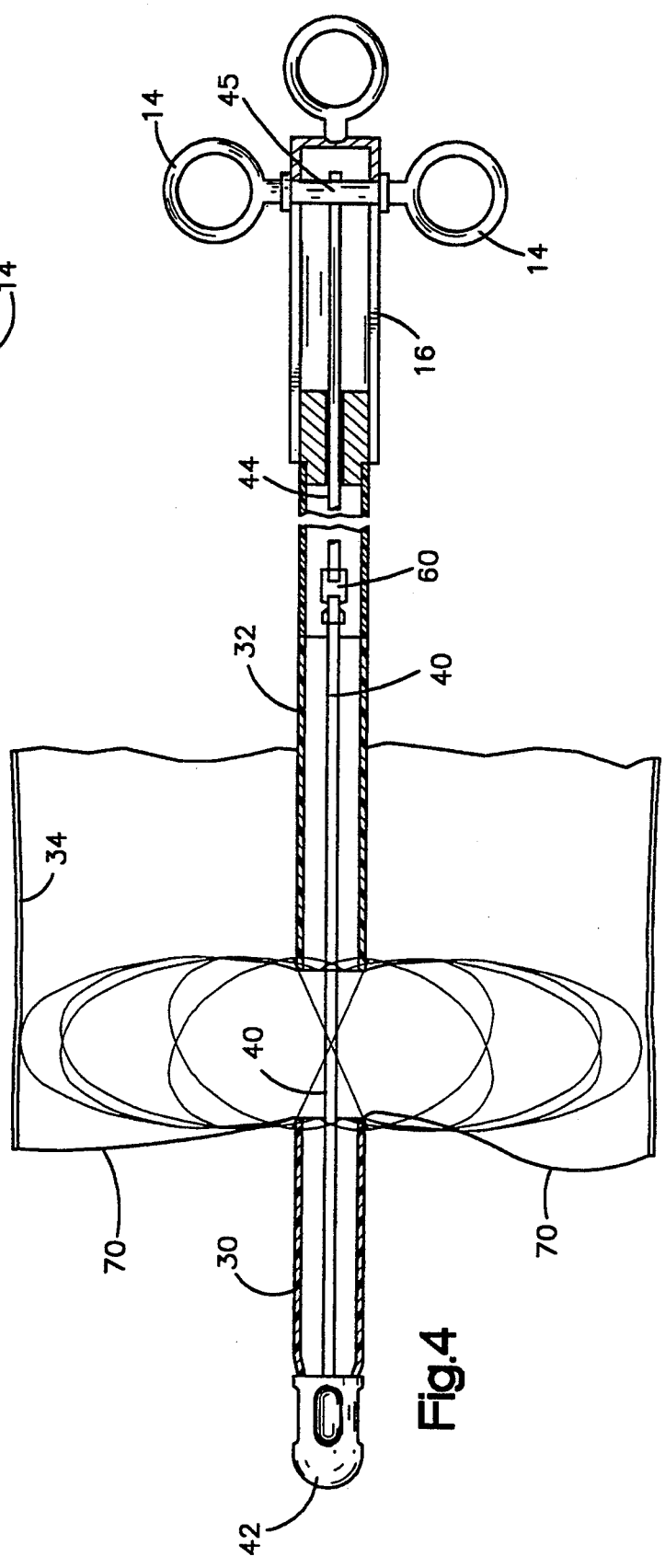

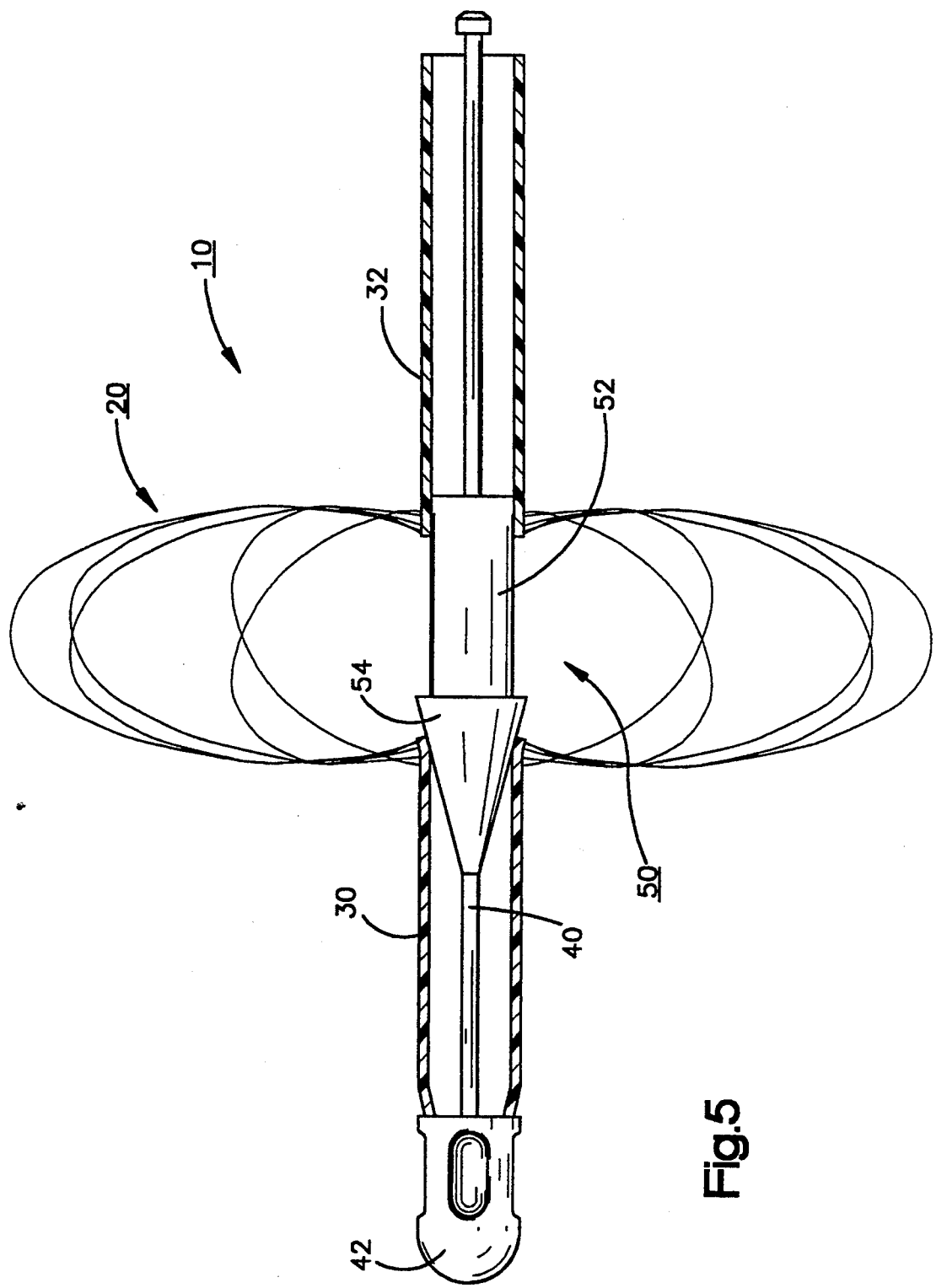

EXPANDABLE TEMPORARY GRAFT

FIELD OF THE INVENTION

The present invention concerns an expandable temporary medical implant particularly suited for use in temporary placement in the abdominal region of the aortic artery.

BACKGROUND ART

One well recognized technique for repair of an aortic aneurism is to surgically repair the aortic artery by cutting out the diseased portion of the artery and replacing it with a prosthetic graft. Various size and shape grafts are well known for use depending upon where the aneurism in the artery occurs. Representative prior art patents that discuss non-surgical repair of an aortic aneurism include U.S. Pat. No. 4,577,631 to Kreamer; U.S. Pat. No. 4,140,126 to Choudhury; and U.S. Pat. No. 4,562,596 to Kornberg. Each of these devices can be inserted into a damaged region by means of catheter inserted into the femoral artery in the patient's leg and routed up the body to the vicinity of the aortic aneurism.

U.S. Pat. No. 5,034,001 to Garrison et al. concerns a vascular catheter, including an expandable wire cage mounted on the distal end of a tubular member. There is no mention in the '001 patent for use of this device in repairing a damaged aortic artery. The expandable wire cage holds open a blood vessel and allows perfusion of blood through the blood vessel.

Experience with sutureless graft replacement of the descending thoracic aorta is discussed in a paper to Oz et al. entitled "Twelve-Year Experience with Intraluminal Sutureless Ringed Graft Replacement of the Descending Thoracic and Thoracoabdominal Aortic" (*Journal of Vascular Surgery*, Volume 11, No. 2, February 1990). A similar development is disclosed in an article to Matsumae et al. entitled "An Experimental Study of a New Sutureless Intraluminal Graft with an Elastic Ring that Can Attach Itself to the Vessel Wall" (*Journal of Vascular Surgery*, July 1988).

In an article entitled "Percutaneously Placed Endovascular Grafts for Aortic Aneurisms Feasibility Study" to Mirich et al., self-expanding endovascular grafts are described for insertion within a region of an aortic aneurism. The article discusses a self-expanding metallic stent covered with a nylon material. The nylon material acts as a support and template for encasement, enabling formation of vascular lumen within the aortic artery. This work is reported in *Radiology*, 1989, Volume 170, Pages 1033–1037.

DISCLOSURE OF THE INVENTION

The present invention concerns an implantable medical device, including an elongated, expandable tubular mesh that can be used to bring a temporary graft into position against an inner wall lining of a blood vessel. The mesh has first and second end portions connected to two flexible, solid tubes that are spaced from each other by an exposed segment of the tubular mesh. A flexible core extends through the tubes and is attached at one end to a further or distalmost tube. This core provides relative movement between the tubes and expands the mesh. The entire device can be inserted and placed in an appropriate region within an aortic artery to temporarily stabilize an aneurism.

As the mesh expands outward due to relative movement of the two flexible, solid tubes toward each other, the implant separates from an elongated implant catheter. A locking device simultaneously fixes the two solid tubes in a position which holds the mesh in its expanded form.

The implantable device is most preferably used in conjunction with a flexible graft that overlies the exposed tubular mesh and is brought into contact with diseased or damaged blood vessel wall linings when the device is expanded. In this preferred arrangement, blood flow through the vessel maintains the graft in its open position. Blood flows through the open wire strands of the expanded mesh and does not significantly impede blood flow.

BRIEF DESCRIPTION OF THE DRAWINGS

FIG. 1 is a perspective view of a medical implant constructed in accordance with the present invention;

FIG. 2 is a perspective view of the FIG. 1 medical device showing an expanded configuration of a wire mesh that brings a graft into contact with a damaged region of a vessel;

FIGS. 3 and 4 are section views of the medical implant of FIG. 1 showing expansion of the wire mesh to bring a graft into engagement with a blood vessel wall; and FIG. 5 is a partially sectioned view of the implant showing a locking device for holding the wire mesh in its expanded position.

BEST MODE FOR PRACTICING THE INVENTION

Turning now to the drawings, FIGS. 1 and 2 depict an implantable medical device 10 particularly suited for temporary placement in the abdominal region of an aortic artery. When placed within the artery, the implant helps stabilize the patient by impeding further degradation in the aneurism. In the preferred application, the temporary placement is supplemented by surgical intervention which allows a more permanent replacement sleeve to be implanted within the patient.

The device 10 is placed within the aortic artery by means of an elongated placement catheter 12 having an elongated, tubular sheath which enters the patient through the femoral artery in the patient's leg. After the implant 10 is properly positioned, the attending physician can release the implant within the subject by pulling on sliding rings 14 attached to a handle 16 used to maneuver the catheter 12 into the subject.

As described more fully below, pulling on the sliding rings 14 causes a wire mesh 20 carried by the implant 10 to expand outwardly. The wire mesh 20 supports a flexible temporary graft, and as the wire mesh 20 expands outwardly, the graft is brought into contact with the inner wall lining of the sortie artery to stabilize the aneurism and inhibit leakage and/or rupturing of the aneurism.

As seen most clearly in FIGS. 3 and 4, the medical implant 10 includes two flexible, elongated tubes 30, 32 that are connected together by the wire mesh 20. The tubes 30, 32 are preferably plastic and formed with the wire mesh 20 imbedded within the plastic. The tubes 30, 32 can be braided or non-braided to add stiffness. In the preferred and disclosed embodiment, the wire mesh 20 extends along the length of the two tubes 30, 32. The two tubes are approximately the same length and each covers approximately one third of the length of the mesh 20 so that approximately one third of the mesh is exposed in the region between the two tubes.

As the exposed portion (see FIG. 4) of the mesh 20 expands, it moves a graft 34 carried by the implant into contact with the inner wall linings of a subject. In order to expand the exposed mesh portion into the configuration shown in FIGS. 2 and 4, the two tubes 30, 32 are pushed toward each other, causing the mesh 20 to expand outwardly and forcing the graft 34 to open and engage the wall linings.

Mesh expansion is most preferably accomplished by means of a center core member 40 that extends axially through the tubes and mesh 20 and is attached to a rounded metal tip 42 by a crimp connection. As seen in FIG. 3, the tip 42 overlies an extreme distal end of the plastic tube 30 and the tip 42 is firmly attached to both the tube 30 and the core member 40.

The core member 40 is an elongated flexible metal rod (preferably stainless steel) which is attached to an elongated flexible actuator rod 44 extending through the catheter 12 and connected to a crosspiece 45 that connects the sliding rings 14 at a proximal end of the catheter 12. A distalmost end of the catheter's tubular sheath has the same diameter as the tube 32 and abuts against one end of the tube 32 so that, as the rings 14 are pulled back by the physician to the position shown in FIG. 4, the actuator 14 pulls on the core member 40, bringing the two tubes 30, 32 closer together and causing the exposed portion of the wire mesh 20 to expand outwardly.

A locking device 50 (FIG. 5) holds the two tubes 30, 32 in fixed position relative to each other after the mesh 20 has expanded into the configuration shown in FIG. 4. The locking device 50 includes a hollow sleeve 52 attached to a distal end of the tube 32 by means of a suitable adhesive such as an adhesive commercially available from Loctite Prism Series 401. A cone-shaped portion 54 of the locking device 50 is attached to the sleeve 52 and includes a base which has a diameter greater than the inner diameter of the tube 30. With the implant device 10 unopened or unexpanded, the cone-shaped portion 54 of the locking device 50 lies beneath the graft 34. As the physician pulls on the sliding rings 14 to retract the core member 40, the plastic tube 30 is retracted toward the cone-shaped member 54 and, as seen in FIG. 5, engages the cone-shaped member 54. Frictional engagement between the proximal end of the tube 30 and the cone-shaped member of the locking device holds the wire mesh 20 in its expanded configuration.

As the locking device 50 is engaged by the tube 30 (see FIG. 5) further movement of the actuator 44 is resisted and the actuator pulls free from the core member 40. A metal coupling 60 connects the actuator 44 and core member 40. One end of the coupling 60 is fused or adhesively secured to the actuator 44. The other end of the coupling 60 is crimped onto the core member 40. As the sliding rings 14 pull back on the actuator 44, relative movement between the catheter 12 and tube 30 is possible until the locking device 50 and tube 30 engage. From then on, further movement of the rings 14 is resisted and the crimp connection of the coupling 60 lets go, allowing the catheter 12 to separate from the medical implant device 10.

Apparatus similar to the catheter 12, handle 16 and sliding rings 14 is described more fully in issued U.S. Pat. No. 4,921,484 to Hillstead. This patent is assigned to the assignee of the present invention and is incorporated herein by reference.

The graft 34 is attached to the tube 30 by means of thin strands 70 of thread which are fused with the tube 30. These strands 70 maintain engagement between the graft 34 and the implant device 10. Once the wire mesh expands to the configuration shown in FIG. 4, the flexible graft opens, at least at its distalmost end, and allows blood flow to enter the graft and expand the graft to its fully opened condition. For this reason, the mesh 20 need only engage one end of the graft since, once the graft's distal end is open, blood flow maintains the graft in contact with the blood walls along the length of the graft.

Alternate embodiments of the invention are envisioned. These include multiple expanded portions of the wire mesh such as, for example, an implant including two spaced wire mesh portions separated by a third tube. Additional uses of the implant 10 would include a caval filter, atrial or ventricular septal defect repair device, a retrieval mechanism or a laser, fiber or ultrasound guidance platform.

The present invention has been described with a degree of particularity. It is the intent, however, that the invention include all modifications from the disclosed design falling within the spirit or scope of the appended claims.

We claim:

1. A medical implant device comprising:
    a pair of axially spaced apart flexible tubes;
    a tubular mesh connected between said tubes, said tubular mesh expandable from a first position to a second position having an outer diameter greater than the outer diameters of said tubes upon relative axial movement of said tubes toward one another;
    a flexible core extending through said tubes and said mesh, said core having an end portion attached to one of said tubes; and
    a locking device located at least partially within the axial extent of said mesh for fixing said tubes in a relative axial position to maintain said mesh in the second position.

2. The medical implant device of claim 1 further including a flexible tubular graft located radially outwardly of said mesh for engaging a wall lining of a vessel when said mesh is in the second position.

3. The medical implant device of claim 2 further including at least one thread having one end connected to one of said tubes and one end connected to said graft.

4. The medical implant device of claim 1 wherein a portion of said mesh is embedded within one of said tubes.

5. The medical implant device of claim 1 wherein said locking device comprises a cone-shaped wedge for frictional engagement with one end of said tube attached to said core to hold said tubes in a relatively spaced condition.

6. The apparatus of claim 1 further including a coupling for connecting an actuator with said core, said coupling separable to permit said core in the medical implant device to release from said actuator as the mesh is expanded to a limit.

7. Apparatus comprising:
    an elongated catheter having a handle at one end attached to a tubular sheath adapted to extend into a subject;
    a medical implant device comprising:

i) a tubular mesh connecting axially spaced apart flexible tubes, said mesh expandable to a diameter greater than the outer diameter of said tubes as the tubes move axially toward one another;

ii) a flexible core extending through said tubes and mesh, said core attached at one end to one of said spaced apart tubes;

iii) a locking device for fixing said spaced apart tubes in a position relative to each other to maintain said mesh in an expanded condition, said locking device located at least partially within said mesh;

a temporary graft overlying said mesh and including an outer surface for engaging an inner wall lining of a blood vessel of the subject when said mesh is in the expanded condition; and an elongated actuator means extending through said catheter sheath for moving said tubes in a direction towards one another to expand said mesh.

8. The apparatus of claim 7 further including a coupling for connecting said actuator means with said core, said coupling separable to permit said core of the medical implant device to release from said actuator means in said catheter sheath as the mesh is expanded to an expansion limit.

9. The apparatus of claim 8 wherein said tubular sheath has an axial end surface for abutting one of said tubes to limit movement of said tube as the other tube is retracted by said core.

10. The apparatus of claim 7 wherein said locking device comprises a cone-shaped member attached to one of said two tubes, said cone-shaped member having a diameter greater than an inside diameter of a distalmost one of said two tubes to frictionally engage an inner surface of said distalmost tube as it is moved toward a proximal one of said tubes by said core.

11. A medical implant device comprising:
a) a pair of axially spaced apart flexible tubes;
b) a tubular mesh connected between two flexible tubes that are axially spaced apart, said tubular mesh is expandable to a diameter greater than a diameter of the two flexible tubes as the tubes move axially toward one another;
c) a flexible core extending through the tubes and attached at one end to one tube, said core passing through said tubular mesh; and
d) a locking device for fixing the solid tubes in a position relative to each other to maintain said mesh expanded towards a wall lining of a vessel into which the medical implant device has been placed, said locking device comprises a cone-shaped wedge that frictionally engages one end of the tube to which the core is attached to hold the two tubes in a axially spaced apart relationship.

12. The medical implant device of claim 11 further including a coupling for connecting said actuator with said core, said coupling separable to permit said core of the medical implant device to release from said actuator in said catheter sheath as the mesh expands outward to an expansion limit.

13. Apparatus comprising:
a) an elongated catheter having a handle at one end attached to a tubular sheath adapted to extend into a subject;
b) a medical implant device comprising:
  i) a tubular mesh connected between to two flexible tubes that are spaced apart by a segment of the tubular mesh which expands to a diameter greater than a diameter of the two flexible tubes as the tubes move axially toward one another;
  ii) a flexible core extending through the tubes and attached at one end to one tube, said core passing through the segment of the tubular mesh; and
  iii) a locking device for fixing the tubes in a relative position to maintain the mesh expanded, said locking device comprises a cone-shaped member attached to one of said two tubes, said cone-shaped member having a diameter greater than an inside diameter of a distalmost one of said tubes to frictionally engage an inner surface of said distalmost tube as it moves toward a proximal one of said tubes;
c) a temporary gaft overlying the segment of the tubular mesh; and
d) elongated actuator means extending through the catheter sheath for moving the tubes towards one another to expand the tubular mesh and graft.

14. The apparatus of claim 13 further including a coupling for connecting said actuator means with said core, said coupling separable to permit said core of the medical implant device to release from said actuator in said catheter sheath as the mesh is expanded outward to an expansion limit.

* * * * *